United States Patent
Chang et al.

(10) Patent No.: US 11,744,450 B2
(45) Date of Patent: Sep. 5, 2023

(54) ORAL IMAGING DEVICE

(71) Applicant: AUO Display Plus Corporation, Hsinchu (TW)

(72) Inventors: Liang-Jen Chang, Hsinchu (TW); Hui-Lung Lu, Hsinchu (TW)

(73) Assignee: AUO DISPLAY PLUS CORPORATION, Hsinchu (TW)

( * ) Notice: Subject to any disclaimer, the term of this patent is extended or adjusted under 35 U.S.C. 154(b) by 72 days.

(21) Appl. No.: 17/505,667

(22) Filed: Oct. 20, 2021

(65) Prior Publication Data

US 2023/0068812 A1 Mar. 2, 2023

(30) Foreign Application Priority Data

Aug. 31, 2021 (TW) .................................. 110132364

(51) Int. Cl.
| | |
|---|---|
| *A61B 1/24* | (2006.01) |
| *G03B 15/03* | (2021.01) |
| *A61B 1/04* | (2006.01) |
| *A61B 1/06* | (2006.01) |

(52) U.S. Cl.
CPC ................ *A61B 1/24* (2013.01); *A61B 1/044* (2022.02); *A61B 1/0625* (2022.02); *G03B 15/03* (2013.01)

(58) Field of Classification Search
CPC ............................ A61B 5/0088; H04N 23/555
See application file for complete search history.

(56) References Cited

U.S. PATENT DOCUMENTS

| | | | | |
|---|---|---|---|---|
| 5,038,258 A | * | 8/1991 | Koch | .................... G01J 3/10 |
| | | | | 362/237 |
| 6,038,024 A | * | 3/2000 | Berner | .................. G01J 3/508 |
| | | | | 356/407 |
| 7,006,126 B2 | * | 2/2006 | Kerschbaumer | ......... A61B 1/24 |
| | | | | 348/66 |
| 8,982,200 B2 | * | 3/2015 | Kitaoka | ................. A61B 1/247 |
| | | | | 348/66 |
| 10,271,732 B2 | * | 4/2019 | Chen | ..................... A61B 1/053 |
| 10,542,928 B2 | * | 1/2020 | Houjou | .................. A61B 5/444 |
| 2006/0152586 A1 | | 7/2006 | Komiya et al. | |
| 2007/0134614 A1 | * | 6/2007 | Weichselbaum | ....... A61B 1/247 |
| | | | | 348/66 |
| 2008/0192235 A1 | | 8/2008 | Komiya et al. | |

(Continued)

FOREIGN PATENT DOCUMENTS

| | | |
|---|---|---|
| CN | 110859682 A | 3/2020 |
| JP | 2006334241 A * | 12/2006 |

*Primary Examiner* — Leon W Rhodes, Jr.
(74) *Attorney, Agent, or Firm* — WPAT, P.C (57) ABSTRACT

An oral imaging device includes a base, a camera module, and a plurality of light source modules. The base includes a camera component, an opening surface, and a plurality of light source components connected to two sides of the camera component. A slant angle exists between each light source component and the camera component. The slant angle is a non-right angle. The opening surface is substantially parallel to the camera component. The camera module is located on the camera component and faces the opening surface. The plurality of light source modules each are located on each light source component and configured to project a light beam onto the opening surface. A center ray of the light beam passes through a center point of the opening surface.

15 Claims, 11 Drawing Sheets

(56) References Cited

U.S. PATENT DOCUMENTS

| | | |
|---|---|---|
| 2009/0067695 A1 | 3/2009 | Komiya et al. |
| 2009/0181339 A1 | 7/2009 | Liang et al. |
| 2011/0221880 A1 | 9/2011 | Liang et al. |
| 2019/0056272 A1 | 2/2019 | Guillot et al. |
| 2020/0395517 A1* | 12/2020 | Tsai ................. H01L 33/502 |

* cited by examiner

ORAL IMAGING DEVICE

CROSS-REFERENCE TO RELATED APPLICATION

This non-provisional application claims priority under 35 U.S.C. § 119(a) to Patent Application No. 110132364 filed in Taiwan, R.O.C. on Aug. 31, 2021, the entire contents of which are hereby incorporated by reference.

BACKGROUND

Technical Field

Provided relates to an imaging device, and in particular, to an oral imaging device.

Related Art

In daily life, in addition to the basic chewing function of teeth, the color and the uniformity of teeth are also concerned. This is because the color and the uniformity of teeth affect impressions to others and self-confidence. A dentist repairs a tooth or an artificial tooth of a subject to maintain the beauty and the chewing function. During the repair of the tooth or the artificial tooth, color matching for the tooth is very important.

In order to achieve optimal repair quality, a color approximately the same as the colors of other teeth is required for the tooth or the artificial tooth. Conventionally, the dentist takes a photograph of the teeth by using a camera, and then performs visual color matching by using a colorimetric card or a colorimetric model. Then, the dentist determines a similar and proper color for the subject according to the experience. However, color standards in the colorimetric card and the colorimetric model both differ from an actual tooth color. In addition, colors in photographs taken under different ambient light sources also differ from the actual tooth color. therefore, the visual color selection, which completely relies on the color sensation of the dentist, leads to chromatic aberration, and also leads to misjudgment of the dental mold factory as a result of the chromatic aberration.

SUMMARY

The instant disclosure provides an oral imaging device. The oral imaging device includes a base, a camera module, and a plurality of light source modules. The base includes: a camera component; a plurality of light source components, connected to two sides of the camera component, where a slant angle exists between each light source component and the camera component, and the slant angle is a non-right angle; and an opening surface, substantially parallel to the camera component. The camera module is located on the camera component and faces the opening surface. The plurality of light source modules each are located on each light source component and configured to project a light beam onto the opening surface. A center ray of the light beam passes through a center point of the opening surface.

In some embodiments, an included angle exists between the light beam and the opening surface, and the included angle is substantially the same as the slant angle.

In some embodiments, the each light source component includes a shielding portion and a recess portion that are connected to each other. The shielding portion is located between the recess portion and the camera component to prevent the light beam from being perpendicularly incident on the camera module.

In some embodiments, the recess portion includes a light hole. The light hole forms a light exit surface of the light beam, and the light beam is projected onto the opening surface through the light exit surface formed by the light hole.

In some embodiments, a relative distance between the camera component and an end of the shielding portion in a direction perpendicular to the camera component is greater than a depth of the recess portion.

In some embodiments, the recess portion includes a first end surface and a second end surface that are opposite to each other, and a curvature of the first end surface is greater than a curvature of the second end surface.

In some embodiments, the each light source component includes a connecting plate and a fixing plate that are connected to each other. The connecting plate connects the camera component to the fixing plate and has disposed thereon the light source module. The opening surface is formed between the fixing plate and the fixing plate of another light source component. The slant angle exists between the connecting plate and the camera component. The fixing plate is substantially perpendicular to the opening surface.

In some embodiments, the each light source component includes a first slot portion, a connecting slot portion, and a second slot portion. The connecting slot portion connects the first slot portion to the second slot portion. Each light source module includes an optical film and a light bar assembly. The optical film is located at the first slot portion, and the light bar assembly is located at the second slot portion.

In some embodiments, the optical film includes a diffusion film and a polarizing film, and the light beam successively passes through the diffusion film and the polarizing film to be projected onto the opening surface.

In some embodiments, a width of the connecting slot portion is less than a width of the first slot portion, and is less than a width of the second slot portion, and wall surface of the first slot portion wraps peripheries on two sides of the optical film, so that a width of a light exit surface of the optical film is less than or equal to the width of the connecting slot portion.

In some embodiments, the each light source component includes a body layer and an anti-reflection layer. The anti-reflection layer is located on a side surface of the body layer that is close to the opening surface.

In some embodiments, the oral imaging device may further include a cushion component. The cushion component includes a plurality of first side portions and a plurality of second side portions. The first side portions are located on sides of the light source components, and the second side portions are connected to the first side portions, so that the cushion component surrounds a periphery of the opening surface.

In some embodiments, the cushion component further includes a plurality of binding members. The base further includes a plurality of positioning members. The binding members are bound to the positioning members, to position the cushion component on the base.

In some embodiments, the cushion component further includes a plurality of occlusion support members. Each occlusion support member is located on one of the first side portions and extends toward another first side portion, or each occlusion support member is located on one of the second side portions and extends toward another second side portion.

In some embodiments, the cushion component further includes a connection portion. The connection portion is connected to the occlusion support members and passes through the center point of the opening surface.

In some embodiments, the oral imaging device further includes a mask. The mask covers the base and exposes the opening surface.

Thus, by means of the oral imaging device of the instant disclosure, the impact of ambient light on the analysis of an image of teeth can be effectively prevented, and the light beam projected by the light source module can have a relatively desirable optical effect, so that the image captured by the camera module has relatively desirable and uniform image quality. In this way, the medical personnel (medical technicians) can obtain the image of the teeth in a same ambient light condition under different ambient light sources, and an aberration of a color in an actual taken image from an actual color of the teeth is reduced. Therefore, the medical personnel (medical technicians) no longer need to determine a tooth color according to the experience, and the misjudgment by a dental mold factory as a result of a chromatic aberration of a colorimetric card can also be avoided. In addition, the oral imaging device of the instant disclosure conforms to the ergonomic design and can be tightly attached to an oral cavity of a subject. Moreover, after the image of the oral cavity is captured, the new cushion component can be immediately replaced with a new one, so that the health of the subject is guaranteed.

Detailed features and advantages of the instant disclosure are described in detail in the following embodiments, which are sufficient for any person skilled in the art to understand the technical content of the instant disclosure and implement the operations accordingly. According to the content disclosed in this specification, the scope of patent application, and the drawings, any person skilled in the art can easily understand related objectives and advantages of the instant disclosure.

DETAILED DESCRIPTION

The following provides detailed descriptions of various embodiments. However, the embodiments are merely used as an example for description and are not intended to limit or reduce the protection scope of the instant disclosure. Well-known elements and steps are not described in the embodiments, to avoid unnecessary limitations to the contents of the instant disclosure. In addition, some elements are omitted in the drawings in the embodiments, to clearly show the technical features of the instant disclosure. The same reference numerals are used to denote the same or similar elements in all of the drawings.

In this specification, unless specifically limited to the article, "a" and "the" may generally refer to a single one or more. It is to be further understood that, "include", "comprise", and similar terms used in this specification refer to recorded features, integers, steps, operations, elements, and/or components, but do not exclude one or more described or extra other features, integers, steps, operations, elements, components, and/or groups thereof.

Figure 1:
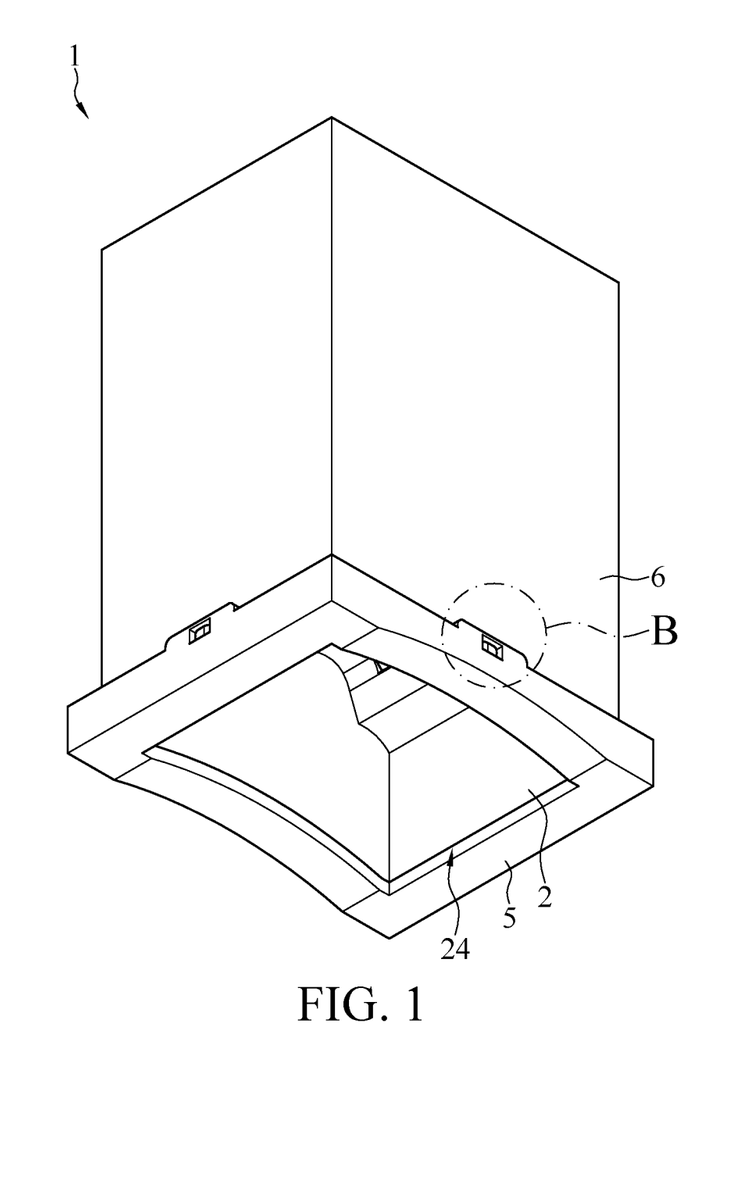
FIG. 1 is a schematic appearance diagram (I) according to an embodiment of the instant disclosure.
Figure 2:
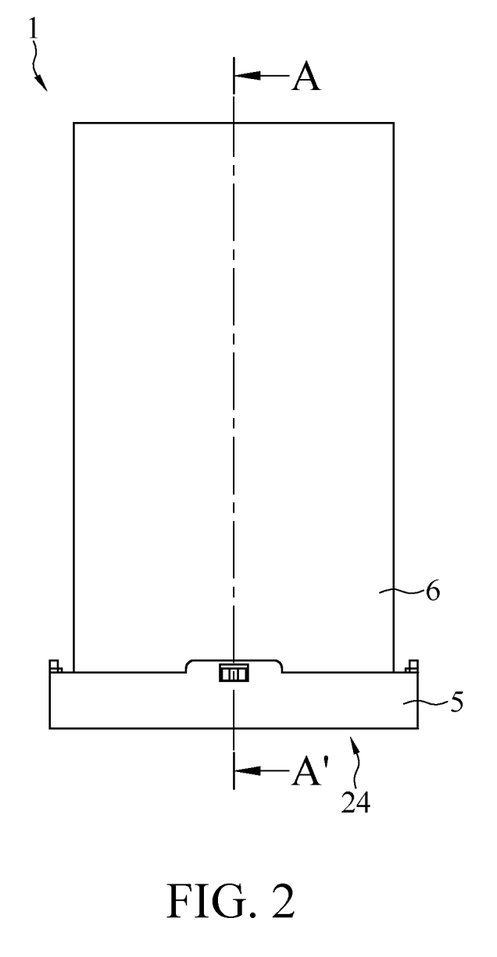
FIG. 2 is a schematic appearance diagram (II) according to an embodiment of the instant disclosure.
Figure 3A:
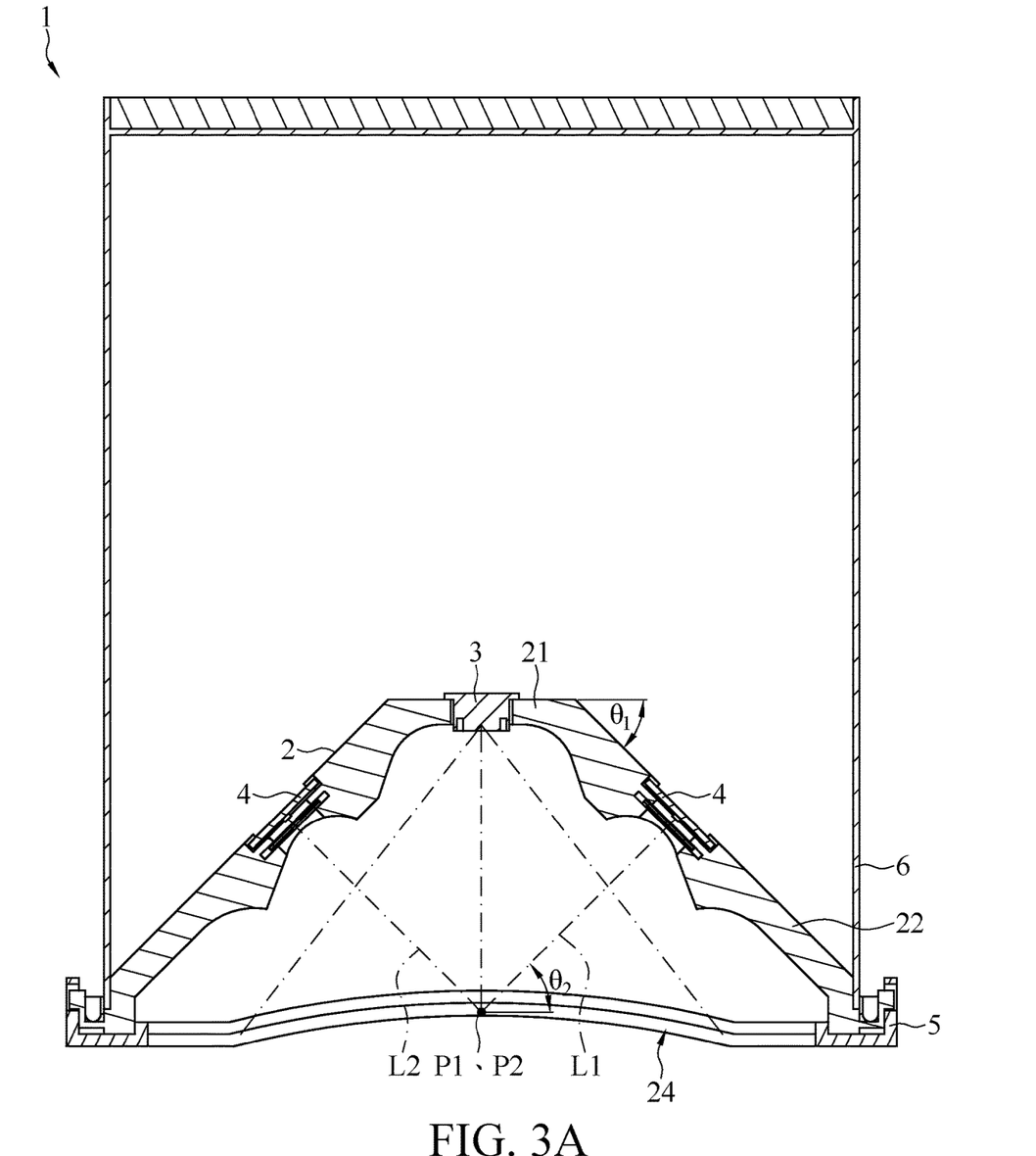
FIG. 3A is a schematic cross-sectional view (I) along a line A-A' in FIG. 2.

Referring to FIG. 1, FIG. 2 and FIG. 3A, FIG. 1 and FIG. 2 are respectively schematic appearance diagrams (I) and (II) according to an embodiment of the instant disclosure, and FIG. 3A is a schematic cross-sectional view (I) along a line A-A' in FIG. 2. An embodiment of the instant disclosure provides an oral imaging device 1. The oral imaging device may mainly include a base 2, a camera module 3, and a plurality of light source modules 4.

The base 2 may mainly include a camera component 21, a plurality of light source components 22, and an opening surface 24. The camera component 21 and the plurality of light source components 22 each may be a plate structure. The plurality of light source components 22 are connected to two sides of the camera component 21. Referring to FIG. 3A, the camera component 21 and the plurality of light source components 22 approximately form a shape like a Chinese character n with lower ends gradually expanding (that is, a shape of a trapezoid). A slant angle $\theta_1$ exists between each light source component 22 and the camera component 21. The slant angle $\theta_1$ is a non-right angle. In some embodiments, the slant angle $\theta_1$ is preferably an acute angle. The slant angle $\theta_1$ is preferably 30 degrees, 45 degrees, or 60 degrees. In the drawings, the slant angle $\theta_1$ is 45 degrees, but the present invention is not limited thereto.

As shown in FIG. 3A, one ends of the plurality of light source components 22 are connected to the camera component 21, and other ends of the plurality of light source components form the opening surface 24. The opening surface 24 is substantially parallel to the camera component 21. A cross section of the base 2 is approximately in a trapezoid shape. The base has a hollow cavity. In other words, the base 2 is overall approximately in a pyramid shape, and is hollow inside, to form an optical reflection cavity, but the present invention is not limited thereto.

The camera module 3 is disposed on the camera component 21, and is configured to capture an image of the opening surface 24. The camera module 3 may be preferably disposed in a center position of the camera component 21, and captures the image by using a center point P2 of the opening surface 24 as a center.

The plurality of light source modules 4 each are disposed on each light source component 22, and each are configured to project a light beam 40 (shown in FIG. 4B) onto the opening surface 24. In other words, the each light source component 22 is equipped with a light source module 4. Center rays L1 and L2 of the light beams, a center point P1 of the image, and the center point P2 of the opening surface 24 are concurrent on a specific plane. The specific plane may be the cross section of A-A' in FIG. 2. Thus, as shown in FIG. 3A, the center rays L1 and L2 of the light beams pass through the center point P2 of the opening surface 24. Specifically, the center rays L1 and L2 of the light beams can pass through the center point P1 of the image and the center point P2 of the opening surface 24.

An included angle $\theta_2$ exists between the light beam and the opening surface 24. The included angle $\theta_2$ is substantially the same as the slant angle $\theta_1$. In some embodiments, the slant angle $\theta_1$ is preferably an acute angle. The included angle $\theta_2$ is preferably an acute angle as well. The slant angle $\theta_1$ and the included angle $\theta_2$ are both preferably 45 degrees. However, the present invention is not limited thereto. Thus, when the included angle $\theta_2$ between the light beam and the opening surface 24 is 45 degrees, the light beams 40 projected by the light source modules 4 on two sides of the camera module 3 both pass through the center point P2 of the opening surface 24, and an included angle between the light beams on two ends is exactly 90 degrees. In this way, homogenization of the light sources is achieved.

Figure 3B:
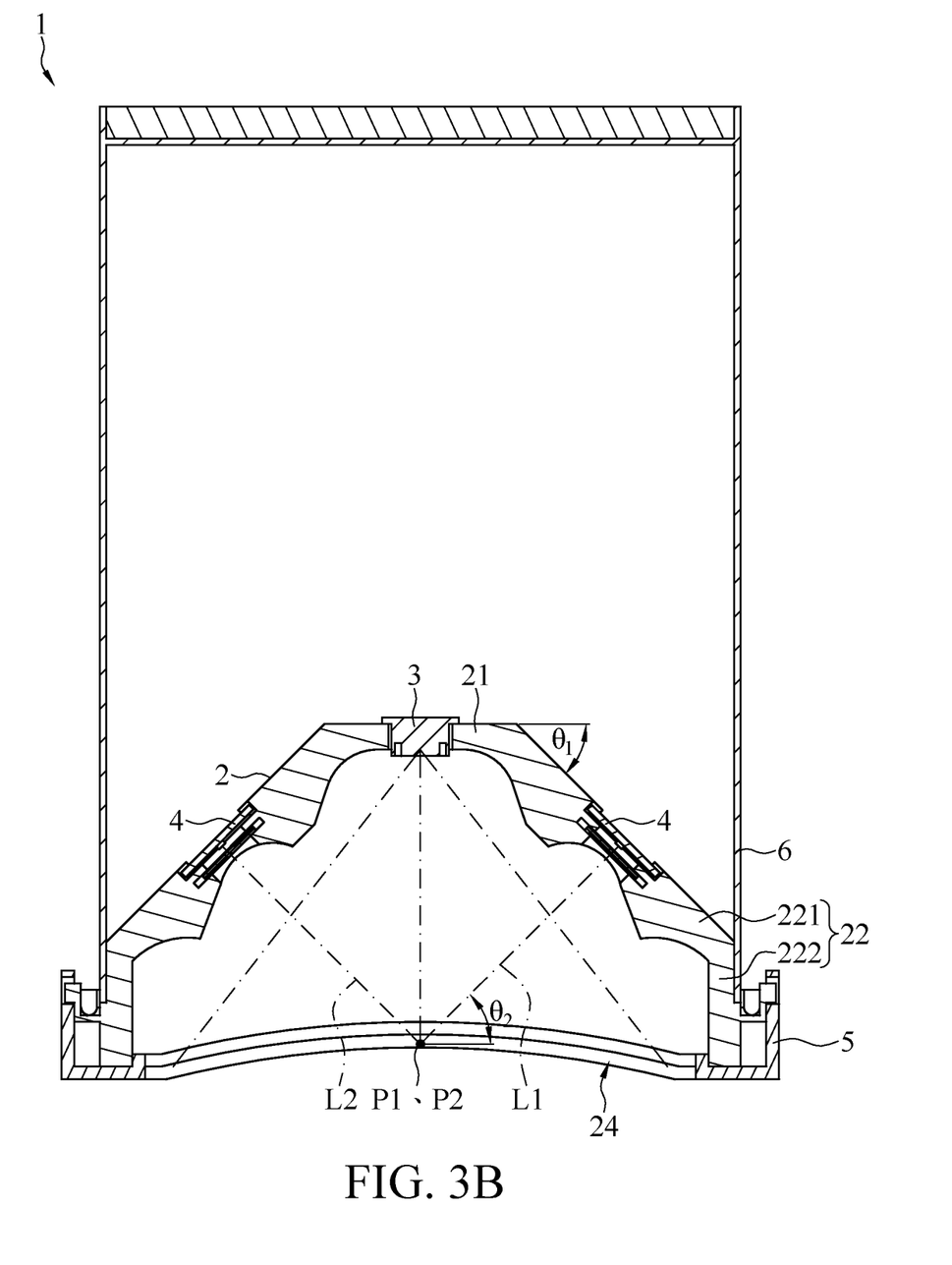
FIG. 3B is a schematic cross-sectional view (II) along the line A-A' in FIG. 2.

In some embodiments, refer to FIG. 3B. FIG. 3B is a schematic cross-sectional view (II) along the line A-A' in FIG. 2. A connecting plate 221 and a fixing plate 222 connected to each other may be further disposed on the each light source component 22. The connecting plate 221 connects the camera component 21 to the fixing plate 222, and has disposed thereon the light source module 4. The opening surface 24 is formed between the fixing plate 222 and the fixing plate 222 of another light source component 22. In this case, a slant angle $\theta_1$ exists between the connecting plate 221 and the camera component 21. The fixing plate 222 is substantially perpendicular to the opening surface 24. As shown in FIG. 3B, the cross section of the base 2 is overall approximately in a hexagon shape. The present invention is not limited thereto. In addition, regardless of the structure shown in FIG. 3A or the structure shown in FIG. 3B, the light beams 40 projected by the light source modules 4 on the two sides of the camera module 3 pass through the center point P2 of the opening surface 24, and the included angle between the light beams on the two ends is exactly 90 degrees.

Figure 4A:
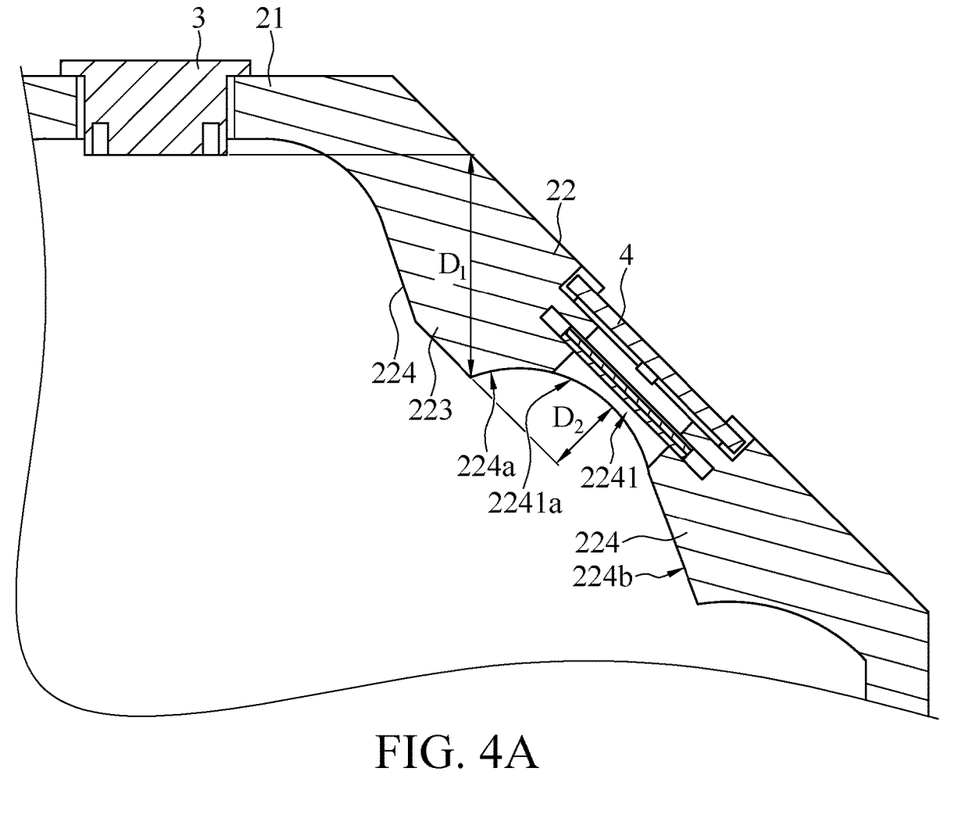
FIG. 4A is a partial enlarged view (I) of the schematic cross-sectional view along the line A-A' in FIG. 2.
Figure 4B:
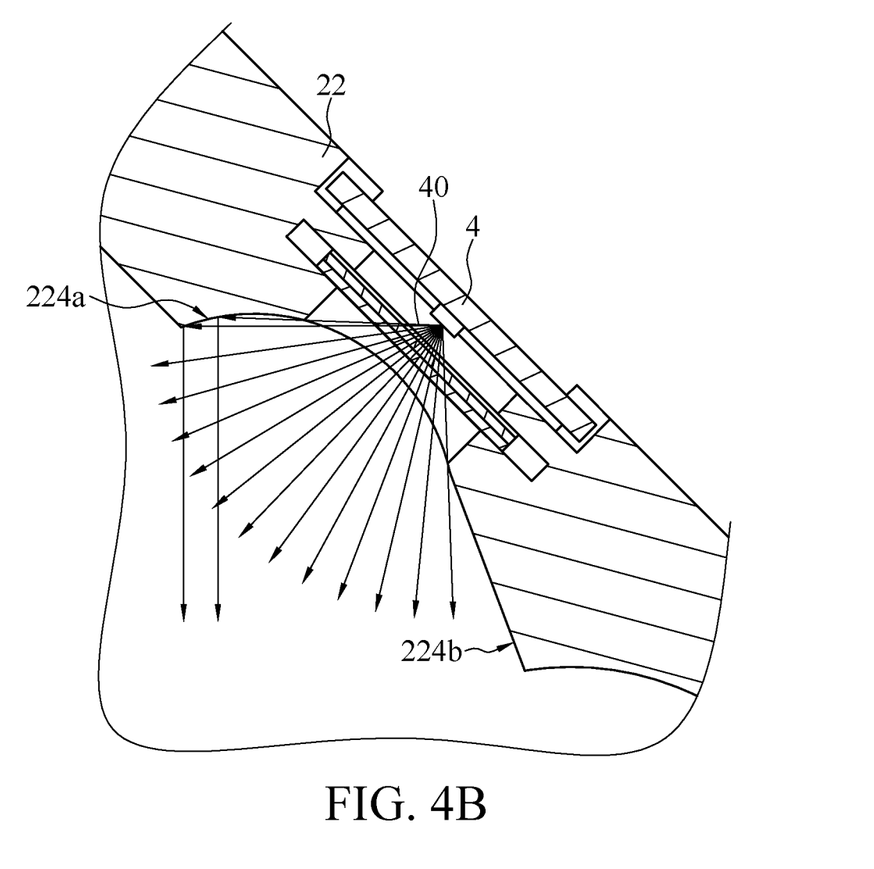
FIG. 4B is a partial enlarged view (II) of the schematic cross-sectional view along the line A-A' in FIG. 2.

In some embodiments, refer to FIG. 4A and FIG. 4B. FIG. 4A and FIG. 4B are respectively partial enlarged views (I) and (II) of the schematic cross-sectional views along the line A-A' in FIG. 2. A shielding portion 223 and recess portions 224 connected to each other may be further disposed on the each light source component 22. The recess portions 224 are respectively disposed on two ends of the shielding portion 223. One of the recess portions 224 is connected to the camera component 21, and the light source module 4 is disposed inside the other of the recess portion 224. A part of the light beam projected by the light source module 4 inside the recess portion 224 is reflected by the shielding portion 223, so as to prevent the light beam from being perpendicularly incident on the camera module 3.

In some embodiments, referring to FIG. 4A, each recess portion 224 may be in an arcuate recessed structure. The recess portion 224 is an asymmetric structure. The recess portion 224 has a first end surface 224a and a second end surface 224b that are opposite to each other. The first end surface 224a is an end close to the camera component 21, and the second end surface 224b is an end away from the camera component 21. In addition, a curvature of the first end surface 224a is greater than a curvature of the second end surface 224b. That is to say, the second end surface 224b is flatter than the first end surface 224a, so that the recess portion 224 is formed into an asymmetric structure. In this way, the light beam projected by the light source module 4 in the recess portion 224 tends to aim at the opening surface 24, as shown in FIG. 4B.

In some embodiments, referring to FIG. 4A, the recess portion 224 has a light hole 2241. The light hole 2241 is located at a bottom of the recess portion 224. The light source module 4 is disposed at a bottom of the light hole 2241. A top of the light hole 2241 forms a light exit surface 2241a for the light beam 40. The light beam 40 is projected onto the opening surface 24 through the light exit surface 2241a formed by the light hole 2241. In other words, the light beam projected by the light source module 4 can be projected onto the opening surface 24 through the light hole 2241. An irradiation range of the light beam projected by the light source module 4 is limited by a wall surface of the light hole 2241.

Since the shielding portion 223 is located between the recess portion 224 and the camera component 21, the camera component 21 is also presented as a recessed structure relative to the shielding portion 223. Therefore, in these recessed structure, a relative distance $D_1$ between the camera component 21 and the shielding portion 223 in a direction perpendicular to the camera component 21 is greater than a depth $D_2$ of the recess portion 224. As shown in FIG. 4A, the relative distance $D_1$ between the camera component 21 and an end of the shielding portion 223 in the direction perpendicular to the camera component 21 is preferably greater than 15 mm. The depth $D_2$ of the recess portion 224 is preferably in a range of 4 mm to 6 mm, and preferably, is about 5 mm.

Figure 5:
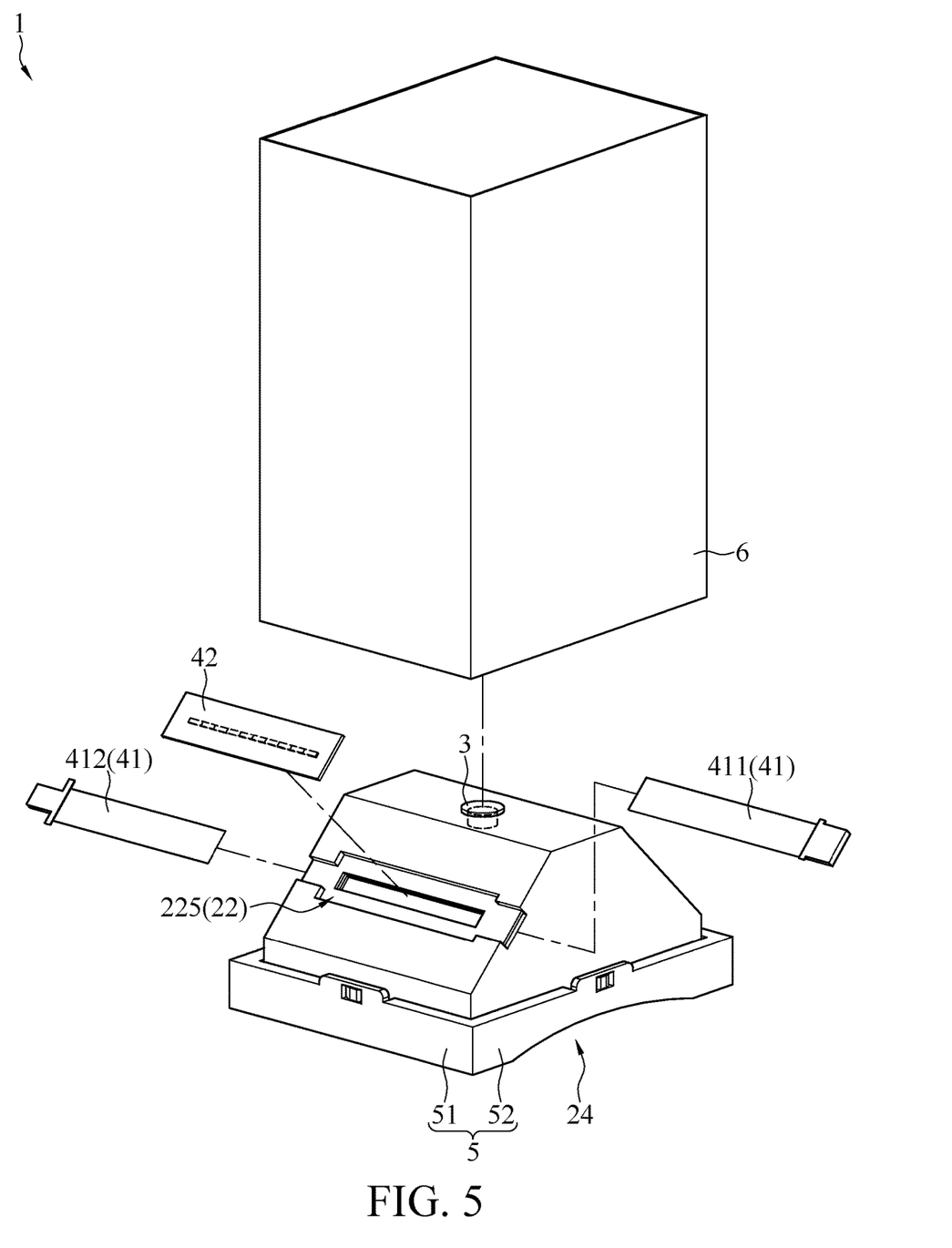
FIG. 5 is a schematic exploded view (I) according to an embodiment of the instant disclosure.
Figure 6:
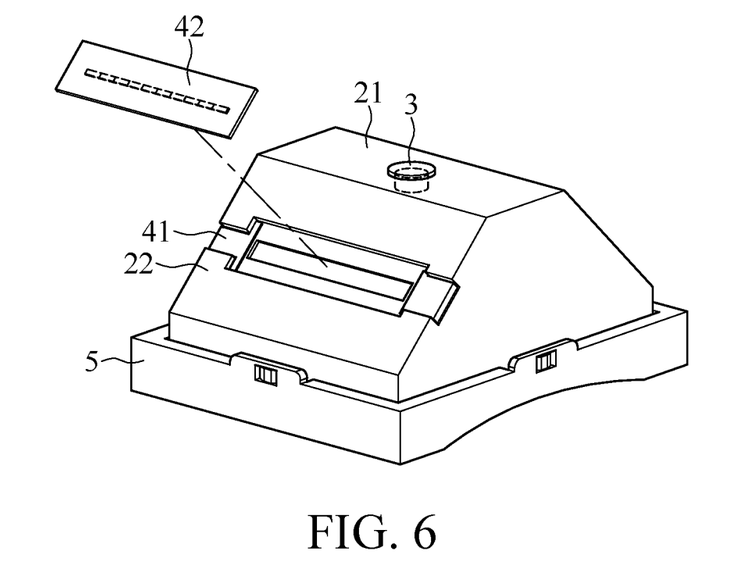
FIG. 6 is a schematic exploded view (II) according to an embodiment of the instant disclosure.
Figure 7:
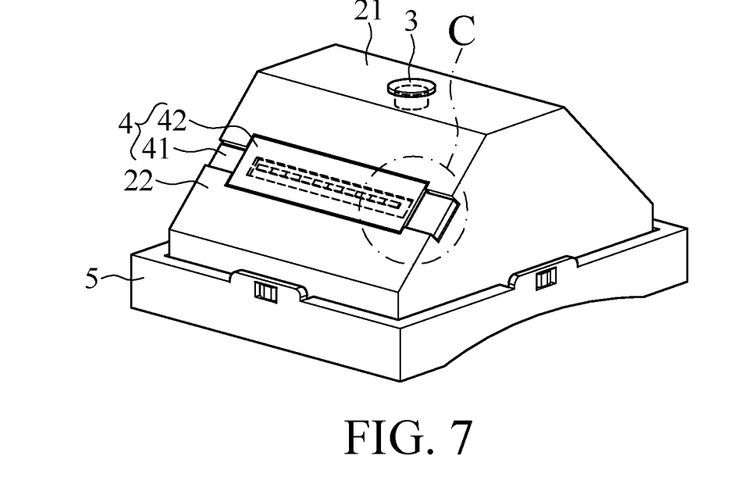
FIG. 7 is a schematic appearance diagram (III) according to an embodiment of the instant disclosure.
Figure 8:
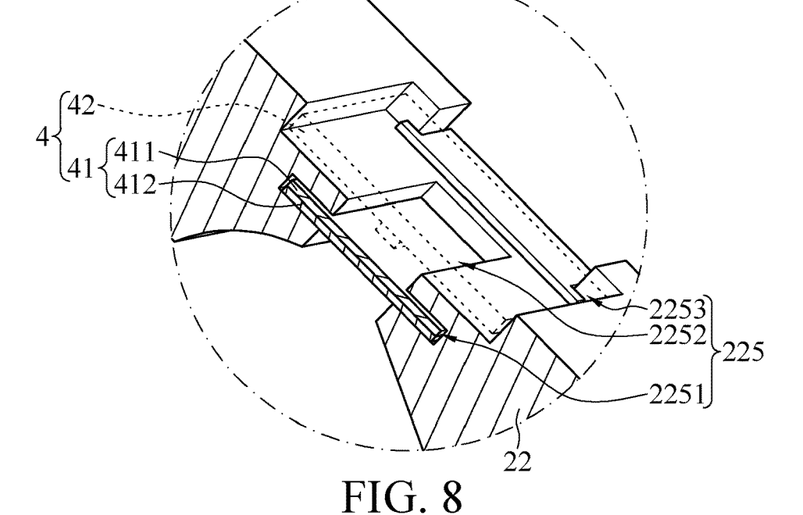
FIG. 8 is a partial enlarged view of C in FIG. 7.

In some embodiments, refer to FIG. 5 to FIG. 8. FIG. 5 and FIG. 6 are schematic exploded views (I) and (II) according to an embodiment of the instant disclosure, FIG. 7 is a schematic appearance diagram (III) according to an embodiment of the instant disclosure, and FIG. 8 is a partial enlarged view of C in FIG. 7. An accommodating slot 225 is further provided on the light source component 22 for mounting the light source module 4. As shown in FIG. 8, the accommodating slot 225 may be composed of a first slot portion 2251, a connecting slot portion 2252, and a second slot portion 2253. The connecting slot portion 2252 may connect the first slot portion 2251 to the second slot portion 2253. The accommodating slot 225 is overall approximately in an I shape (or an H shape). The light source module 4 may be composed of an optical film 41 and a light bar assembly 42. The optical film 41 is disposed on the first slot portion 2251. The light bar assembly 42 is disposed on the second slot portion 2253, and projects a light beam onto the optical film 41 inside the first slot portion 2251.

In some embodiments, further refer to FIG. 5 to FIG. 8. The optical film 41 may be composed of a diffusion film 411 and a polarizing film 412. The diffusion film 411 is close to the second slot portion 2253, and the polarizing film 412 is away from the second slot portion 2253, so that the light beam successively passes through the diffusion film 411 and the polarizing film 412 to be projected onto the opening surface 24.

In some embodiments, referring to FIG. 6 to FIG. 8, a width of the first slot portion 2251 is substantially the same as a width of the second slot portion 2253. A width of the connecting slot portion 2252 is less than the width of the first slot portion 2251, and is less than the width of the second slot portion 2253 as well. A wall surface of the first slot portion 2251 wraps peripheries on two sides of the optical film 41, so that a width of a light exit surface of the optical film 41 is less than or equal to the width of the connecting slot portion 2252. In other words, the peripheries on the two sides of the optical film 41 are completely accommodated in the first slot portion 2251, so that an edge of the optical film 41 is not exposed. In this way, not only the optical film 41 is positioned, but also light leakage can be prevented.

In some embodiments, an inner wall surface (facing the opening surface 24) of the light source component 22 may be black or dark-colored. In some embodiments, the light source component 22 includes a body layer and an anti-reflection layer (not shown in the figure). The anti-reflection layer is located on a side surface of the body layer that is close to the opening surface 24, that is, the anti-reflection layer may be coated on the inner wall surface of the light source component 22. Thus, the light beam 40 (shown in FIG. 4B) projected by the light source module 4 can achieve a relatively desirable optical effect, and impact of ambient light on image capture of the camera module 3 is prevented, so that the image captured by the camera module 3 has relatively desirable image quality.

In some embodiments, referring to FIG. 5, a cushion component 5 may be further disposed on the oral imaging device 1. The cushion component 5 is composed of a plurality of first side portions 51 and a plurality of second side portions 52. Two ends of each first side portion 51 are connected to the second side portions 52. Two ends of each second side portion 52 are connected to the first side portions 51. Thus, the cushion component 5 is overall approximately in a rectangle shape. The plurality of first side portions 51 are located on sides of the light source components 22. The plurality of second side portions 52 are connected to the plurality of first side portions 51, so that the cushion component 5 surrounds a periphery of the opening surface 24. In addition, an outer side of each second side portion 52 has an arcuate structure, so that the cushion component 5 has a double arcuate structure, which conforms to the ergonomic design and can be tightly attached to an oral cavity of a subject.

The cushion component 5 may be made of a silica gel material. The cushion component 5 may be preferably a disposable medical-grade silicone cushion. Thus, after the oral imaging device 1 is sleeved in the oral cavity of the subject and captures an image of the oral cavity, the new cushion component 5 can be immediately replaced with a new one, so that the health of the subject is guaranteed.

Figure 9A:
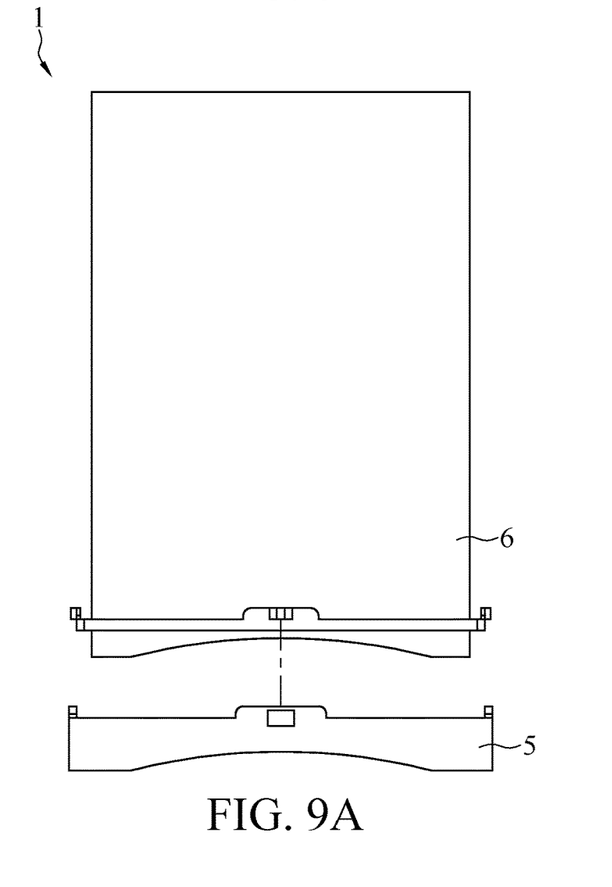
FIG. 9A is a schematic exploded view (III) according to an embodiment of the instant disclosure.
Figure 9B:
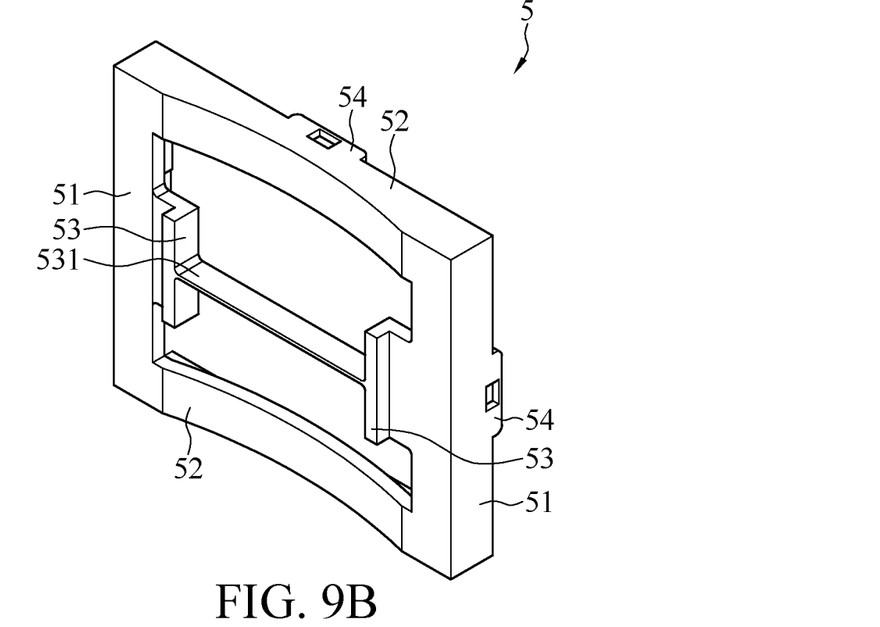
FIG. 9B is a schematic appearance diagram (I) of a cushion component according to an embodiment of the instant disclosure.
Figure 9C:
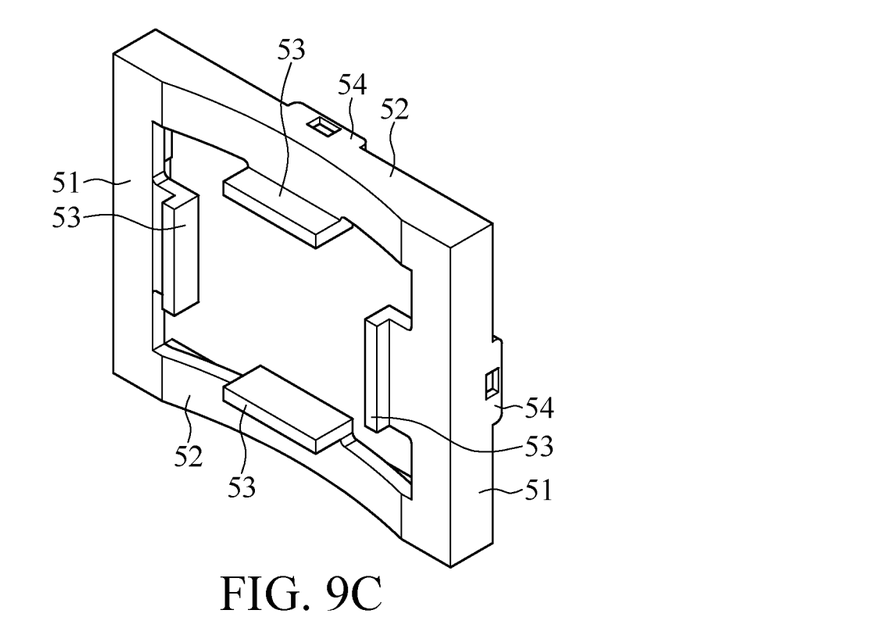
FIG. 9C is a schematic appearance diagram (II) of the cushion component according to an embodiment of the instant disclosure.

In some embodiments, refer to FIG. 9A to FIG. 9C. FIG. 9A is a schematic exploded view (III) according to an embodiment of the instant disclosure. FIG. 9B and FIG. 9C are schematic appearance diagrams (I) and (II) of a cushion component according to an embodiment of the instant disclosure. A plurality of occlusion support members 53 may be further disposed on the cushion component 5. As shown in FIG. 9B, each occlusion support member 53 is located on one of the first side portions 51 and extend toward another first side portion 51. The occlusion support member 53 may be directly formed by extending the first side portion 51. In some embodiments, a connection portion 531 may be further disposed on the cushion component 5, and is connected to the plurality of occlusion support members 53. The connection portion 531 may be directly formed by extending the plurality of occlusion support members 53. The connection portion 531 passes through the center point of the opening surface 24. In this way, the occlusion support members 53 can support the mouth of the subject, and the connection portion 531 may be used for the occlusion of the teeth of the subject, so that the accurate alignment of the teeth of the subject in the image can be achieved, and the light beam projected by the light source module 4 can be precisely irradiated on the teeth of the subject. As shown in FIG. 9C, each occlusion support member 53 may also be located on one of the second side portions 52 and extends toward another second side portion 52. The each occlusion support member 53 may be directly formed by extending the each second side portion 52.

Figure 10:
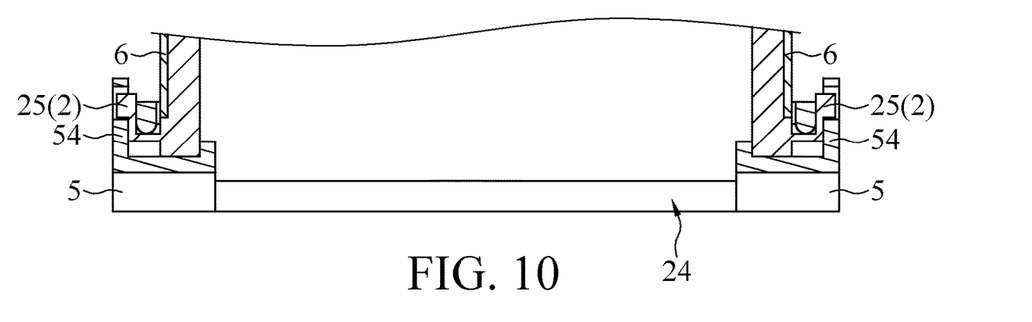
FIG. 10 is a partial enlarged view (III) of the schematic cross-sectional view along the line A-A' in FIG. 2.
Figure 11:
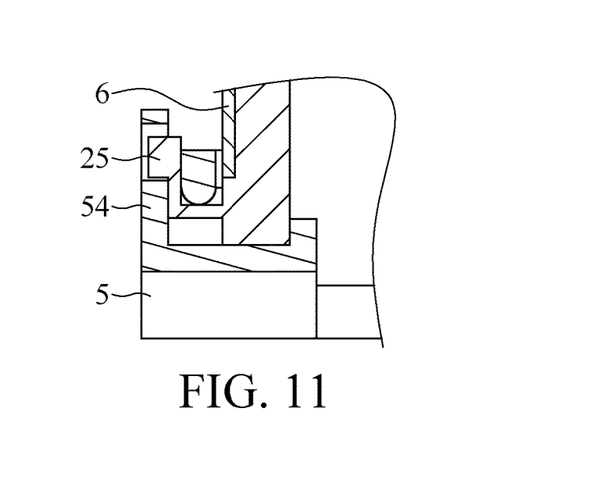
FIG. 11 is a partial enlarged view (IV) of the schematic cross-sectional view along the line A-A' in FIG. 2.
Figure 12:
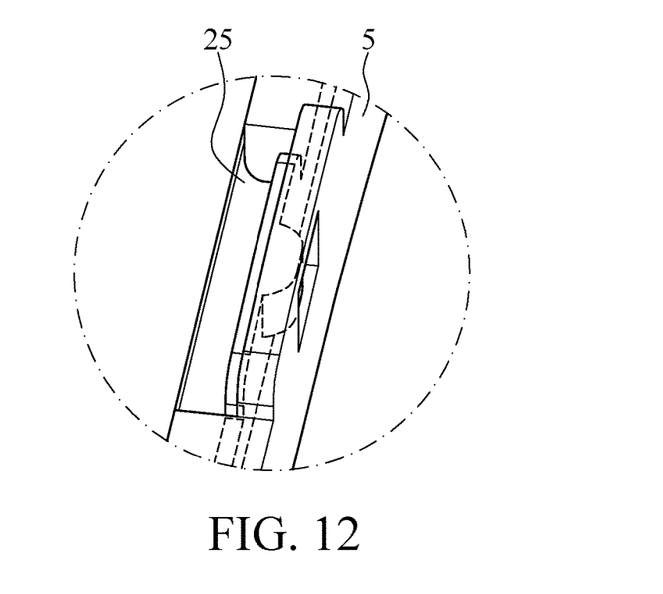
FIG. 12 is a partial schematic enlarged view of B in FIG. 1.

In some embodiments, refer to FIG. 10 to FIG. 12. FIG. 10 and FIG. 11 are respectively partial enlarged views (III) and (IV) of the schematic cross-sectional views along the line A-A' in FIG. 2. FIG. 12 is a partial enlarged view of B in FIG. 1. A plurality of binding members 54 may be further provided on the cushion component 5. A plurality of positioning members 25 may be further provided on the base 2. The cushion component 5 is positioned on the base 2 by bonding the binding members 54 to the positioning members 25. As shown in FIG. 10 and FIG. 11, each binding member 54 may be a channel structure, and each positioning member 25 may be in a buckle structure formed by extending an outer wall surface of the base 2. Thus, when the cushion component 5 is sleeved on the opening surface 24 of the base 2, the positioning member 25 is inserted through the binding member 54 to be buckled with the binding member 54, so as to position the cushion component 5 on the base 2.

In some embodiments, referring to FIG. 1, FIG. 2, and FIG. 5, a mask 6 may be further disposed on the oral imaging device 1. The mask 6 is a long hollow body, and covers the base 2 and exposes the opening surface 24.

In conclusion, by means of the oral imaging device 1 of the instant disclosure, the impact of the ambient light on the analysis of the image of teeth can be effectively prevented, and the light beam 40 projected by the light source module 4 can have a relatively desirable optical effect. For example, the base 2 is approximately a hollow pyramid, to form an optical reflection cavity, and the shielding portion 223 and the recess portion 224 are disposed, so that the image captured by the camera module 3 has relatively desirable and uniform image quality. In this way, the medical personnel (medical technicians) can obtain the image of the teeth in a same ambient light condition under different ambient light sources, and an aberration of a color in an actual taken image from an actual color of the teeth is reduced. Therefore, the medical personnel (medical technicians) no longer need to determine a tooth color according to the experience, and the misjudgment by a dental mold factory as a result of a chromatic aberration of a colorimetric card can also be avoided. In addition, the oral imaging device 1 of the instant disclosure conforms to the ergonomic design and can be tightly attached to an oral cavity of a subject. Moreover, after the image of the oral cavity is captured, the cushion component 5 can be immediately replaced with a new one, so that the health of the subject is guaranteed.

Although the instant disclosure has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. An oral imaging device, comprising:
   a base, comprising:
      a camera component;
      a plurality of light source components, connected to two sides of the camera component, wherein a slant angle exists between each light source component and the camera component, and the slant angle is a non-right angle, wherein the each light source component comprises a shielding portion and a recess portion that are connected to each other, and the shielding portion is located between the recess portion and the camera component; and
      an opening surface, substantially parallel to the camera component;
   a camera module, located on the camera component and facing the opening surface; and
   a plurality of light source modules, each located on each light source component and configured to project a light beam onto the opening surface, wherein a center ray of the light beam passes through a center point of the opening surface.

2. The oral imaging device according to claim 1, wherein an included angle exists between the light beam and the opening surface, and the included angle is substantially the same as the slant angle.

3. The oral imaging device according to claim 1, wherein the recess portion comprises a light hole, the light hole forms a light exit surface of the light beam, and the light beam is projected onto the opening surface through the light exit surface formed by the light hole.

4. The oral imaging device according to claim 1, wherein a relative distance between the camera component and an end of the shielding portion in a direction perpendicular to the camera component is greater than a depth of the recess portion.

5. The oral imaging device according to claim 1, wherein the recess portion comprises a first end surface and a second end surface that are opposite to each other, and a curvature of the first end surface is greater than a curvature of the second end surface.

6. The oral imaging device according to claim 1, wherein the each light source component comprises a connecting plate and a fixing plate that are connected to each other, the connecting plate connects the camera component to the fixing plate and has disposed thereon the light source module, the opening surface is formed between the fixing plate and the fixing plate of another light source component, the slant angle exists between the connecting plate and the camera component, and the fixing plate is substantially perpendicular to the opening surface.

7. The oral imaging device according to claim 1, wherein the each light source component comprises a first slot portion, a connecting slot portion, and a second slot portion, the connecting slot portion connects the first slot portion to the second slot portion, each light source module comprises an optical film and a light bar assembly, the optical film is located at the first slot portion, and the light bar assembly is located at the second slot portion.

8. The oral imaging device according to claim 7, wherein the optical film comprises a diffusion film and a polarizing film, and the light beam successively passes through the diffusion film and the polarizing film to be projected onto the opening surface.

9. The oral imaging device according to claim 7, wherein a width of the connecting slot portion is less than a width of the first slot portion, and is less than a width of the second slot portion, and a wall surface of the first slot portion wraps peripheries on two sides of the optical film, so that a width of a light exit surface of the optical film is less than or equal to the width of the connecting slot portion.

10. The oral imaging device according to claim 1, wherein the each light source component comprises a body layer and an anti-reflection layer, and the anti-reflection layer is located on a side surface of the body layer that is close to the opening surface.

11. The oral imaging device according to claim 1, further comprising: a cushion component, comprising a plurality of first side portions and a plurality of second side portions, wherein the first side portions are located on sides of the light source components, and the second side portions are connected to the first side portions, so that the cushion component surrounds a periphery of the opening surface.

12. The oral imaging device according to claim 11, wherein the cushion component further comprises a plurality of binding members, the base further comprises a plurality of positioning members, and the binding members are bound to the positioning members, to position the cushion component on the base.

13. The oral imaging device according to claim 11, wherein the cushion component further comprises a plurality of occlusion support members, each occlusion support member is located on one of the first side portions and extends toward another first side portion, or each occlusion support member is located on one of the second side portions and extends toward another second side portion.

14. The oral imaging device according to claim 13, wherein the cushion component further comprises a connection portion, and the connection portion is connected to the occlusion support members and passes through the center point of the opening surface.

15. The oral imaging device according to claim 1, further comprising: a mask, covering the base and exposing the opening surface.

* * * * *